(12) United States Patent
Heavner (10) Patent No.: US 10,656,151 B2
(45) Date of Patent: May 19, 2020

(54) AIR CAPILLARY VENT FOR A LATERAL FLOW ASSAY DEVICE

(71) Applicant: Ortho-Clinical Diagnostics, Inc., Raritan, NJ (US)

(72) Inventor: David A. Heavner, Fairport, NY (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 402 days.

(21) Appl. No.: 15/417,833

(22) Filed: Jan. 27, 2017

(65) Prior Publication Data

US 2017/0219576 A1 Aug. 3, 2017

Related U.S. Application Data

(60) Provisional application No. 62/289,140, filed on Jan. 29, 2016.

(51) Int. Cl.
*G01N 33/558* (2006.01)
*B01L 3/00* (2006.01)

(52) U.S. Cl.
CPC .......... *G01N 33/558* (2013.01); *B01L 3/5023* (2013.01); *B01L 3/502723* (2013.01); *B01L 3/502746* (2013.01); *B01L 2200/025* (2013.01); *B01L 2200/0684* (2013.01); *B01L 2300/0816* (2013.01); *B01L 2300/0825* (2013.01); *B01L 2300/0883* (2013.01); *B01L 2300/0887* (2013.01); *B01L 2300/161* (2013.01); *B01L 2400/0406* (2013.01); *B01L 2400/0694* (2013.01); *B01L 2400/082* (2013.01)

(58) Field of Classification Search
None
See application file for complete search history.

(56) References Cited

U.S. PATENT DOCUMENTS 8,025,854 B2 9/2011 Ohman et al.
8,753,585 B2 6/2014 Ohman et al.
(Continued)

FOREIGN PATENT DOCUMENTS

WO WO 03/103835 A1 12/2003
WO WO 2005/089082 A2 9/2005
(Continued)

OTHER PUBLICATIONS

International Search Report and Written Opinion for PCT/US2017/015547; dated May 4, 2017; 10 pages.

*Primary Examiner* — Rebecca L Martinez
(74) *Attorney, Agent, or Firm* — K&L Gates LLP; Louis C. Cullman; Brian J. Novak (57) ABSTRACT

A lateral flow diagnostic assay device is defined by a substrate having a top surface that further includes a sample addition zone for receiving a sample, a transport and reaction zone, and a wicking zone. Each of the sample addition zone, reaction and transport zone and wicking zone are disposed on the top surface of the substrate and fluidically interconnected by means that permit lateral capillary flow along at least one fluid flow path from the sample addition zone to the wicking zone. The assay device further includes a capillary vent disposed in relation to the wicking zone, the capillary vent having an overall length and cross sectional area that creates a backpressure so as to control the flow rate of a sample applied to the assay device.

13 Claims, 7 Drawing Sheets

(56) References Cited

U.S. PATENT DOCUMENTS

| | | | |
|---|---|---|---|
| 8,759,115 B2 | 6/2014 | Ohman et al. | |
| 2004/0189311 A1* | 9/2004 | Glezer | B01L 3/5027 324/444 |
| 2006/0285996 A1 | 12/2006 | Ohman et al. | |
| 2014/0134653 A1 | 5/2014 | Ding et al. | |
| 2014/0141527 A1 | 5/2014 | Ding et al. | |
| 2016/0041163 A1 | 2/2016 | Ding et al. | |

FOREIGN PATENT DOCUMENTS

| | | |
|---|---|---|
| WO | WO 2005/118139 A1 | 12/2005 |
| WO | WO 2006/137785 A1 | 12/2006 |
| WO | WO 2007/149042 A1 | 12/2007 |
| WO | WO 2016/014905 A1 | 1/2016 |

* cited by examiner

AIR CAPILLARY VENT FOR A LATERAL FLOW ASSAY DEVICE

CROSS REFERENCE TO RELATED APPLICATION

This application claims priority under relevant portions of 35 USC § 119 and 37 CFR § 1.53 to U.S. Patent Application No. 62/289,140, filed Jan. 29, 2016. The entire contents of this application is herein incorporated by reference.

TECHNICAL FIELD

This application relates generally to lateral flow diagnostic assay devices and more specifically to a lateral flow diagnostic assay device that includes a capillary vent for purposes of increasing assay sensitivity.

BACKGROUND

Lateral flow diagnostic assay devices are used to detect the presence or absence of at least one specific analyte in a patient's specimen or sample. In some cases, the device is configured to generate a quantitative measure of the amount of a particular analyte. For example, reference is herein made to U.S. Pat. No. 8,753,585, which is hereby incorporated by reference in its entirety.

Lateral flow assay devices are typically defined by a non-porous substrate having a planar upper or top surface having at least three (3) major zones that are formed thereon, namely: (1) a sample addition zone, (2) a transport and detection zone, and (3) a wicking zone. The sample addition zone is typically disposed at one end of the assay device and configured to receive a sample or specimen. The transport and reaction zone, in which the reaction required for the assay occurs, is typically disposed at an intermediate location on the assay device. Finally the wicking zone, which provides the majority of the media that instills capillary flow of the received sample is typically located at an end of the assay device opposite to that of the sample addition zone. The above-noted zones are each fluidically coupled to one another and define at least one fluid flow path.

In typical lateral flow assay devices, the capacity of the assay device is accurately determined by the volume that is defined by the wicking zone. When sample is added in excess, the volume subjected to the assay will always be identical, due to the well-defined and reproducible non-porous structure of the assay device. The sample flow rate in turn can be influenced and controlled by proper selection of the dimensions of the substantially capillary media, the physical properties of the media, as well as by adjusting the chemical, biological or physical properties of the media, e.g., by coating the media with a suitable compound. In some configurations, the flow rate can also be adjusted by selecting a hydrophilic tape for covering the wicking zone of the device and adjusting the properties thereof.

One problem that is presented by existing lateral flow assay devices, once the above-noted physical structure of the device has been set, is that the physical properties of the sample or specimen, such as viscosity or density, is highly influential in determining the sample or specimen flow rate. This influence means that for varying types of samples or specimens, e.g., blood as opposed to urine, completely different physical layouts of the individual lateral flow devices must be designed in order to produce a sample or specimen flow rate that results in adequate sensitivity. The sample or specimen flow rate determines the amount of reaction time, and in general, the greater the reaction time, the greater the sensitivity of the assay.

The foregoing noted effects can thereby possibly lead to greater imprecision of assay results, due to varying reaction times. As a result, there is a general need in the field to provide an improved lateral flow assay device that is more capable of standardization.

BRIEF DESCRIPTION

The present application provides a modification to existing lateral flow assay devices such that the physical layout of the devices can effectively be standardized and other means can therefore be used in order to regulate the flow rate of sample or specimen through the device and thereby increase the sensitivity of the assay. According to one version, a configurable sinuous or tortuous capillary vent is provided that creates a backpressure against the incoming sample or specimen, thereby restricting the escape of air in the lateral flow assay device, which subsequently controls the sample or specimen flow rate.

Provision of the capillary vent permits variations in sample or specimen viscosity or density (or other physical properties of the specimen or sample) to have minimum impact upon the flow rate of sample or specimen in the lateral flow assay device. That is, the implementation of the sinuous capillary vent overrides the influence of viscosity or flow rate in critical flow regions of the assay device, thereby resulting in significantly less variation in sample or specimen flow rate and improved assay sensitivity.

According to one aspect, there is described a lateral flow diagnostic assay device comprising a non-porous substrate having a top surface, a sample addition zone for receiving a liquid sample, a transport and reaction zone and a wicking zone. Each of the sample addition zone, transport and reaction zone and wicking zone are disposed upon the top surface of the substrate and fluidically interconnected to one another by means that permit lateral capillary flow of the liquid sample along at least one fluid flow path from the sample addition zone to the wicking zone. The herein described assay device further includes a capillary vent that is disposed in relation to the wicking zone, the capillary vent having an overall length and cross-section that creates a backpressure so as to control the flow rate of a sample applied to the assay device.

In one version, the capillary vent can be defined by a tubular cross-section that is partially described by a hydrophilic layer covering the wicking zone as well as the capillary vent, the latter extending to the end of the assay device in order to permit the release of air to the atmosphere.

In at least one version, at least a portion including the wicking zone of the the fluid flow path of the assay device can include a plurality of projections formed within the top surface of the substrate. The projections can be sized in terms of their height and cross section, as well as their center to center spacing so as to induce spontaneous capillary flow of an applied liquid sample to the wicking zone.

According to another aspect, there is described a method for controlling the flow rate of a lateral flow diagnostic assay device, the method comprising the steps of providing a substrate, providing a fluid flow path on a top surface of the substrate that includes a wicking zone adjacent one end and a capillary vent extending from an end of the wicking zone, the vent being defined by a cross section and length that permits a backpressure to be developed in order to control the flow of sample in the assay device.

The capillary vent can be configured so as to standardize an assay device.

Additionally, the assay device can further include at least one feature that permits the length and placement of the hydrophilic cover in order to vary the length of the capillary vent. This at least one feature would allow developers to select an appropriate capillary vent for different fluid types, or to specifically "fine tune" the damping characteristics of the assay device. In one version, the at least one feature is an alignment marker disposed on the device.

Other features and advantages will be readily apparent from the following Detailed Description, which should be read in conjunction with the accompanying drawings.

DETAILED DESCRIPTION

The following describes embodiments of a lateral flow diagnostic assay device that is configured with a capillary vent in accordance with at least one described embodiment. It will be readily apparent to those in the field that other variations and modifications to this design can be contemplated to those of adequate skill in the field.

For purposes of this discussion, the term "sample" or "specimen" refers to a volume of a liquid, solution or suspension, intended to be subjected to qualitative or quantitative determination of any of its properties, such as the presence or absence of an analyte, the concentration of an analyte, or other determination. The sample or specimen may be a sample or specimen taken from an organism, such as a mammal, preferably a human; or from the biosphere, such as a water sample, or an effluent; or from a technical, chemical or biological process, such as a process of manufacturing, e.g., the production of medicaments, food, feed, or the purification of drinking water or the treatment of waste effluents. The sample or specimen may be subjected to qualitative or quantitative determinations as such, or after suitable pretreatment, such as homogenization, sonication, filtering, sedimentation, centrifugation, heat treatment or the like.

The term "analyte" refers to any substance that can be measured quantitatively or qualitatively. For example, the presence of an analyte can be determined optically.

The terms "lateral flow device", "lateral flow assay device" and "lateral flow diagnostic assay device" for purposes of this discussion are intended to be used synonymously and refer to a device that employs fluidic flow, such as capillary flow, in a lateral direction of a sample along a defined fluid flow path, the sample undergoing reaction and having an analyte of interest that can be detected.

The term "assay" refers to the qualitative or quantitative reported result for the analyte being measured.

The term "hydraulic radius" refers to a characterization of conduits or vents of circular or non-circular (tubular) cross section in which the hydraulic radius is defined as the cross sectional area of the conduit or vent divided by the perimeter of the cross section. In the embodiments specifically described herein, the cross section of the conduit is circular but under this definition and description that follows, the cross section need not be as limited in scope.

The terms "area" and "zone" are used synonymously herein and refer to a portion of a lateral flow assay device, as described, that is intended for a specific function. For example, the lateral flow assay device may include among others, a sample addition area or zone, a reaction or transport area or zone, and a wicking area or zone.

The terms "distal" and "proximal" for purposes of this discussion refer to opposing respective ends of the lateral flow assay device and are further used to define a frame of reference in conjunction with the accompanying drawings for purposes of describing various components of the lateral flow assay device.

First and for purposes of background, there are several forms of assay devices presently found in the medical diagnostic field used for determining a specific analyte of a bodily fluid sample, such as whole blood, by reacting the fluid sample with at least one reagent and then determining an analyte or marker of interest. For example and referring to FIG. 1, there is shown a known lateral flow assay device 1 defined by a substrate 6, which is substantially planar and further defined by an upper or top surface 7, the substrate forming a support. A plurality of projections 12 extend upwardly from the top surface 7. These projections 12 are disposed in a predetermined spaced relation to one another and dimensioned so as to induce lateral capillary force upon a liquid sample that is introduced into the assay device 1. The assay device 1 is further defined by a plurality of areas or zones that are linearly disposed along at least one fluid flow path. More specifically, the assay device 1 includes a sample addition zone 2 adjacent at least one reagent zone 3, the reagent zone 3 having a detection material (not shown), such as a detection conjugate that is coated, impregnated or otherwise applied or deposited onto the projections 12. A flow channel 4 extends from the reagent zone 3 to an absorbing or wicking zone 5 that is disposed at the opposing end of the fluid flow path relative to the sample addition zone 2. Each of the above noted zones according to this design include a plurality of the projections 12 in order to induce lateral capillary flow through the assay device 1, and more specifically along the defined fluid flow path. Additional specifics relating to this lateral flow assay device can be found in U.S. Pat. No. 8,025,854 B2, WO2003/103835, WO2005/089082, WO2005/118139, and WO2006/137785, all of which are incorporated herein by reference in their entireties.

Figure 1:
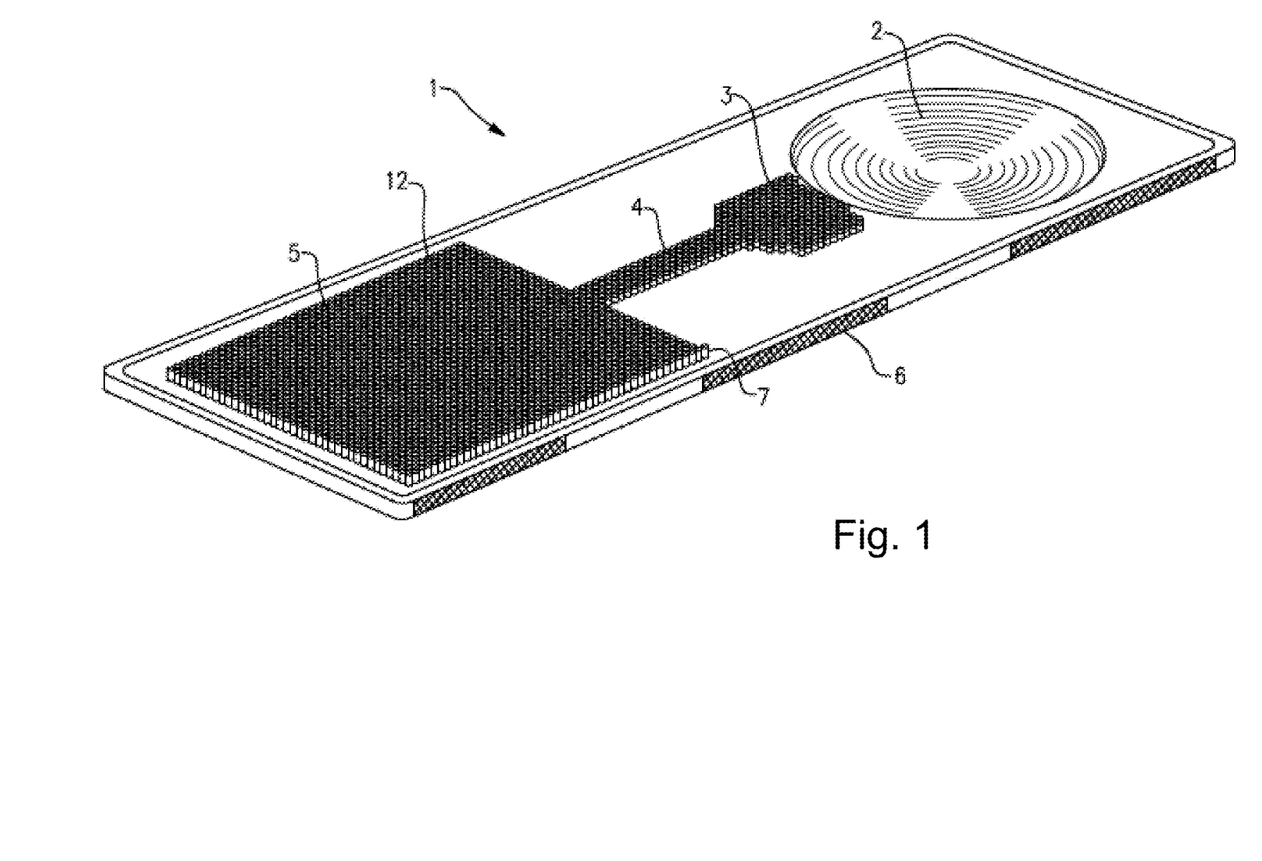
FIG. 1 is a perspective top plan view of a known lateral flow diagnostic assay device.

In terms of overall operation, a fluidic sample such as whole blood is initially applied to the sample addition zone 2 through a cover (not shown) or through direct application using a pipette (not shown) or other dispensing means, wherein sample is caused to move along the defined fluid flow path through the reagent zone 3 based on the capillary pressure exerted by the plurality of projections 12. The sample upon encountering the detection material in the reagent zone 3 which, upon contact, therewith produces a detectable signal, such as a color change that is visually perceivable. The sample, along with the gradually dissolved detection material, continues to migrate through the assay device 1 along the defined fluid flow path through the flow channel 4, the latter having at least one predetermined area or zone configured for detection by an instrument, such as a scanning fluorimeter, and wherein the sample continues to move along the fluid flow path to the absorbing zone 5. After a sufficient time to fill the absorbing zone 5, the assay is considered to be complete and a detectable result can be obtained at the predetermined detection area(s) using the detection instrument.

Figure 2:
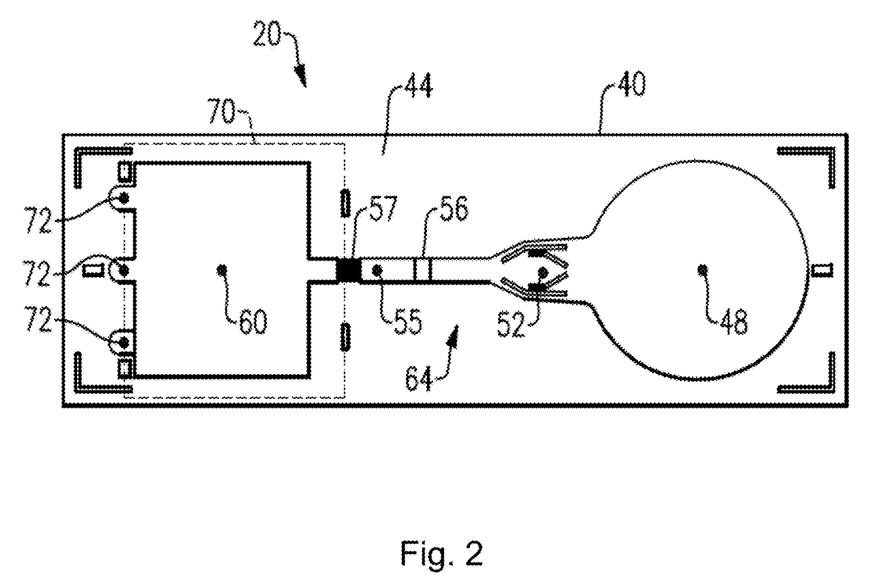
FIG. 2 is a top plan view of another known lateral flow diagnostic assay device.
Figure 3:
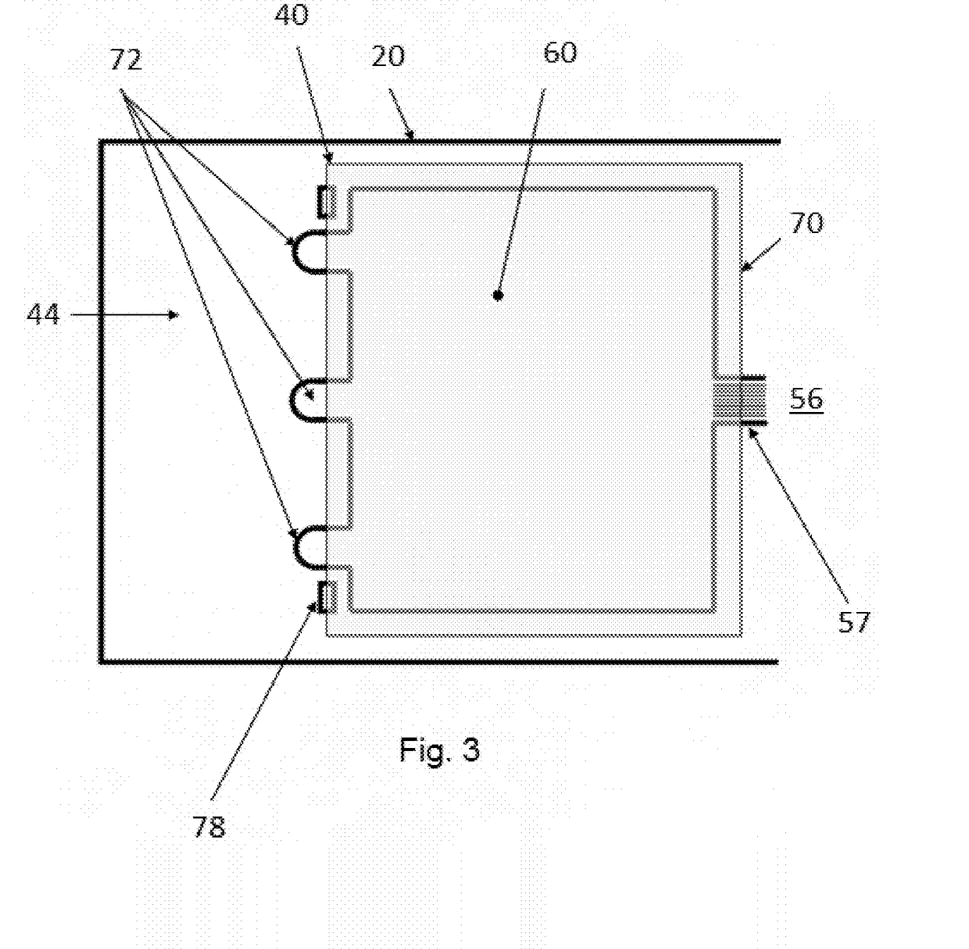
FIG. 3 is an enlarged top plan view of an end portion of the lateral flow diagnostic assay device of FIG. 2.

Another example or version of a lateral flow assay device 20 is illustrated in FIGS. 2 and 3, the assay device 20 including a planar substrate 40 which can be made from a moldable plastic or other suitable non-porous material. The substrate 40 is defined by a top or upper surface 44, which is further defined by a plurality of discrete zones or areas including a sample receiving zone 48, a reagent zone 52, and an absorbing or wicking zone 60. According to this known device design, each of the above-noted zones are fluidically connected to one another in a linear fashion along a defined fluid flow path that further includes a flow channel 64, which can include at least one detection zone (not shown) and in which a plurality of projections (not shown), similar to those provided in the assay device 1 of FIG. 1, are disposed within at least one of the zones and/or the flow channel 64, the projections extending upwardly from the upper surface 44 of the substrate 40 and in which the projections may be provided in at least one or all of the disposed zones of the assay device 20 to promote sample flow.

The projections can be sufficiently dimensioned so as to spontaneously induce capillary flow without the need for additional structure (i.e., side walls, cover or lid) or the application of any externally applied forces. According to this design, a defined fluid flow path is created from the sample receiving zone 48 extending to the wicking zone 60 and in which the fluid flow path is at least partially open. In another embodiment, the assay device 20 can be entirely open. By "open" what is meant is that there is no cover or lid which is maintained at a distance that would contribute to capillary flow. Thus a lid, if present as physical protection for the flow path and the device 20, does not contribute to the capillary flow produced along the fluid flow path. In this known assay device 20, a hydrophilic layer 70 is adhesively or otherwise applied to the top of the projections in the wicking zone 60 in order to increase fluid flow in the assay device 20 and in which a plurality of vents 72 are further defined in the hydrophilic foil layer 70. The hydrophilic layer 70 can include a foil or tape with a hydrophilic adhesive and/or can be made from a hydrophilic material. A flow bridging structure 57 made up of a series of parallel capillary channels may be optionally provided to further enable flow across an outer edge of the hydrophilic layer 70 via the flow channel 64. As in the preceding, this device design employs an open lateral flow path which is further described, including the defined projections, in the following published application: WO2003/103835; WO2005/089082; WO2005/118139; WO2006/137785; and WO2007/149042 as well as U.S. Patent Application Publication No. 2014/0141527 A1, each of which are herein incorporated by reference in their entireties. More specifically, the extending projections each have a height (H), diameter (D) and a distance or distances between the projections (t1, t2) such that lateral capillary flow of an applied fluid, such as plasma, preferably human plasma, can be achieved. These latter relationships are further discussed in U.S. Patent Application Publication No. 2006/0285996, which is further incorporated herein by reference in its entirety.

In use, the assay device 20 operates similarly to the assay device 1, FIG. 1, in which a sample is applied to the sample receiving zone 48, which causes sample to move under capillary force to the reagent zone 52 containing the deposited detection material. When wetted by the sample, the detection material may react, depending on the type of assay (e.g., competitive, sandwich, etc.) with the sample and dissolves, thereby producing a visually perceivable (colored) signal. The sample and the dissolved detection material advance along the defined fluid flow path along the flow channel 64 via the projections and under capillary force into the wicking zone 60. When the wicking zone 60 is filled with fluid, the assay is assumed to be completed and the assay results can be taken by a detection instrument (e.g., a fluorimeter) relative to the flow channel 64 and at least one detection zone 56. The flow path of the herein described device is essentially linear, but could further be defined by a curved or other suitably shaped configuration, as described by way of example in U.S. Patent Application Publication No. 2016/0041163, the entire contents of which are herein incorporated by reference.

According to at least one version, the wicking zone 60 can include projections that are smaller in terms of width and relative spacing as compared to other projections provided in other areas of the device 20 in to provide greater capillary force. The formation and design of the projections, as well as additional details concerning the herein described lateral flow assay device 20 is described in greater detail in U.S. Pat. Nos. 8,753,585, 8,025,854, 8,759,115, U.S. Patent Application Publication Nos. 2006/0285996 and 2014/0134653 each herein incorporated in their entirety by reference.

As noted, the hydrophilicity of the hydrophilic layer 70 improves the capillary flow into the wicking zone 60, as well as provides a cover therefor. At least one vent 72 is placed or positioned adjacent the terminus of the wicking zone 60 such that the sample or specimen flow is not hampered by air back-pressure. Though three (3) vents 72 are shown in FIGS. 1 and 2, the number of vents can be suitably varied. Additionally, the top surface 40 of the assay device 20 can include at least one feature 78, FIG. 2, to aid in the positioning of the edge of the hydrophilic layer 70

More specifically and according to this depicted example, the vents 72 to atmosphere is beyond the terminus of the wicking zone 60 and allows the escape of air as the flow proceeds from the sample addition zone 48 to the wicking zone 60 along the defined fluid flow path or channel 64 following the addition of sample or specimen (not shown). The vents 72 are designed, according to this depicted version, to permit air to escape from the device 20 itself wherein the assay device 20 relies upon flow rate that dependent upon both the physical properties of the device and the physical properties of the sample or specimen, among other major factors.

Certain shortcomings are created using the above-described assay device design. First, the assay device 40 may only be used for one sample or specimen type, for example, blood, urine, or other bodily fluids. Second, the sample or specimen flow rates varies according to the physical properties (i.e., viscosity, density) of the sample or specimen, which may cause considerable variation in the sample or specimen flow rate. Sample or specimen flow rate variation is undesirable in that this variation results in a variable (non-constant) reaction time, which may impact the assay analytical result.

Figure 4:
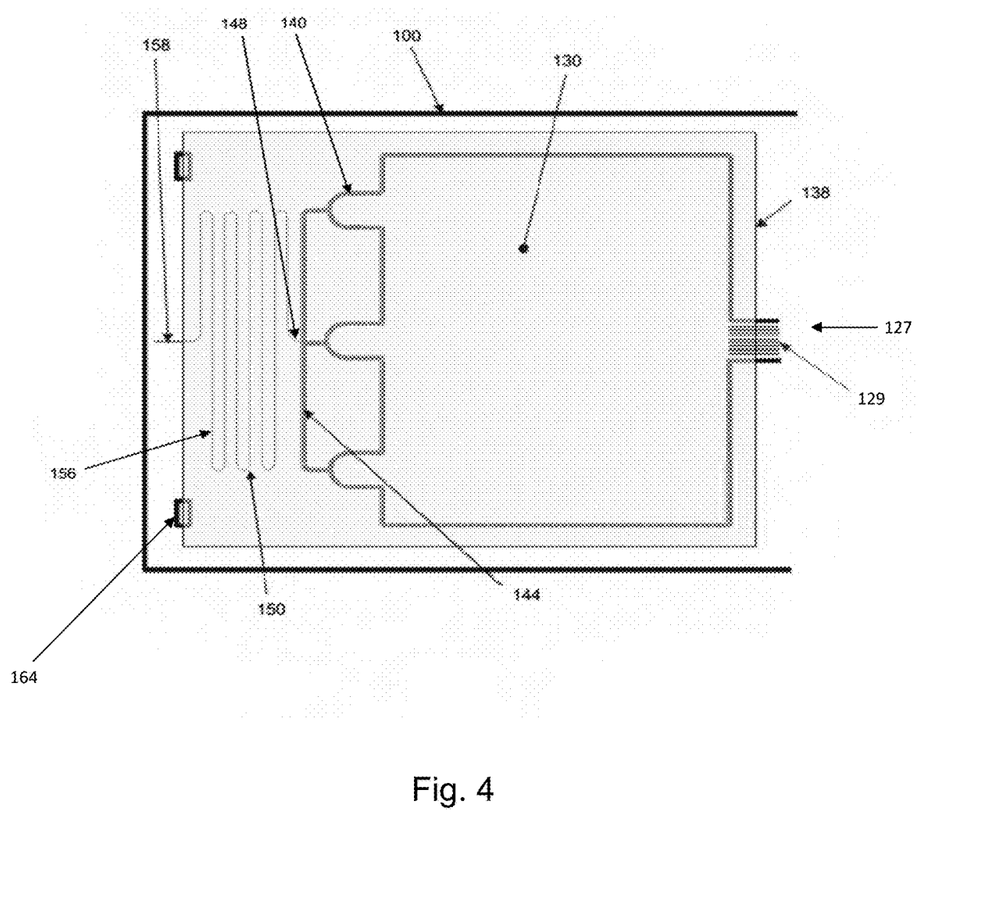
FIG. 4 is a top plan view of a portion of a lateral flow diagnostic assay device made in accordance with an embodiment of the invention, including a capillary vent made in accordance with one version.

Referring to FIG. 4, a lateral flow diagnostic assay device 100 made in accordance with an embodiment of the invention is designed as a modification to the device design according to FIGS. 2 and 3 and more specifically modifying the end section of the assay device shown in FIG. 3. Accordingly, the device 100 is similarly defined by a substrate 114 having a substantially planar top surface 118 on which a sample addition zone, a reaction or transport zone and a wicking zone 130 are individually formed. It will be readily apparent, however, that the assay device 100 herein described is one specific example. That is, the present invention can be utilized in any assay device relying upon lateral fluidic flow occurs over a defined flow path between discrete zones for purposes of determining the presence or concentration of at least one analyte. For purposes of this discussion and though the sample addition zone and reaction or transport zone are not shown in this view, they are intended to be similar if not identical to that previously described, wherein the above noted zones are fluidically connected to define a fluid flow path and can further include a bridging structure 129 to aid the flow of sample into the wicking zone 130.

As in the preceding and for purposes of this specific construction, the substrate 114 of the assay device 100 is made from a non-porous material, such as plastic, in which the sample addition zone is formed at one end (e.g., the proximal end) of the assay device 100. A reaction or transport zone is provided at an intermediate portion of the herein described assay device 100 and the wicking zone 130 is disposed in relation to an end (e.g., the distal end) of the device opposite that of the sample addition zone. In addition, a hydrophilic layer 138 is adhesively or otherwise attached so as to cover the entire wicking zone 130, as well as a peripheral surrounding portion of the wicking zone 130. According to one example, a plurality of projections or microposts, such as shown in FIG. 1, can be provided in the top surface 118 of the substrate 114, and more specifically in each of the zones defining the fluid flow path. The projections can be defined with dimensions (height and width), as well as center to center spacing so as to spontaneously induce lateral capillary flow without requirement of external forces or a cover or lid. Moreover, the dimensions of the projections can be varied so to vary the degree of capillary flow in the assay device 100. More specific details relating to the projections are provided in U.S. Pat. Nos. 8,753,585, 8,025,854, 8,759,115, U.S. Patent Application Publication Nos. 2006/0285996 and 2014/0134653 each previously incorporated in their entirety by reference.

Still referring to FIG. 4, a plurality of vents 140 are disposed in spaced relation at the terminus of the wicking zone 130, each of the vents 140 being interconnected with one another through a series of vent channels 144 that extend between the distal end of the wicking zone 130 and an entrance port 148 of a capillary vent 150 into which the vent channels 144 are merged, according to this embodiment. As discussed herein, the series of vent channels 144 are defined with a sufficiently large cross-section so as not to create backpressure, but sufficiently sized to create an optional manifold that aids in the removal of trapped air, which is then conveyed to the capillary air vent 150. Though this configuration depicts the vent channels 144 as being interconnected, the vents 140 can be separately and independently disposed for connection to the capillary air vent 150.

Located between the distal end of the assay device 100 and the distal end of the wicking zone 130 is the capillary air vent 150, which is defined by a tubular or other suitable cross section, as well as an overall length extending between the entrance port 148 and an exit port 158 that creates backpressure against the flow of sample added to the assay device 100.

The capillary air vent 150 is defined by a sinuous configuration according to this embodiment having a series of tortuous turns or bends 156 extending in a back and forth manner in a direction that is substantially transverse to the fluid flow path 127, as extending between the entrance port 152 and exit port 158 of the capillary vent 150. The exit port 158 extends to the atmosphere from the distal end of the assay device 100 and beyond the peripheral portion of the wicking zone 130 that is covered by the peripheral layer 138. According to this described version, the vent 150 is defined by a total of eight (8) bends 156, though it will be readily apparent that this parameter can be varied provided an adequate overall length of the vent is created.

Still referring to FIG. 4 and as previously noted, each of the existing vents 140 are tied together by vent channels 144 having a sufficient cross sectional area so as not to create any significant backpressure when fluid is entering into the wicking zone 130. The larger cross section vent channels 144 connect to the much smaller cross sectional area channel 144 with a significant length forming the capillary air vent 150. The long overall length and small cross sectional area of the capillary air vent 150 according to the present invention is intended to create a significantly large pressure when sample fluid is flowing into the wicking zone 130 to counteract the capillary pressure driving the flow, thus slowing the flow down. The hydrophilic layer 138 provides the "lid" or $4^{th}$ wall of both the capillary vent 150, as well as the connecting vent channel 144 of the optional manifold. The exit port 158 of the defined capillary air vent 150 emerges from beneath the hydrophilic layer 138, thus providing the vent 150 an exit point to atmosphere.

Figure 5:
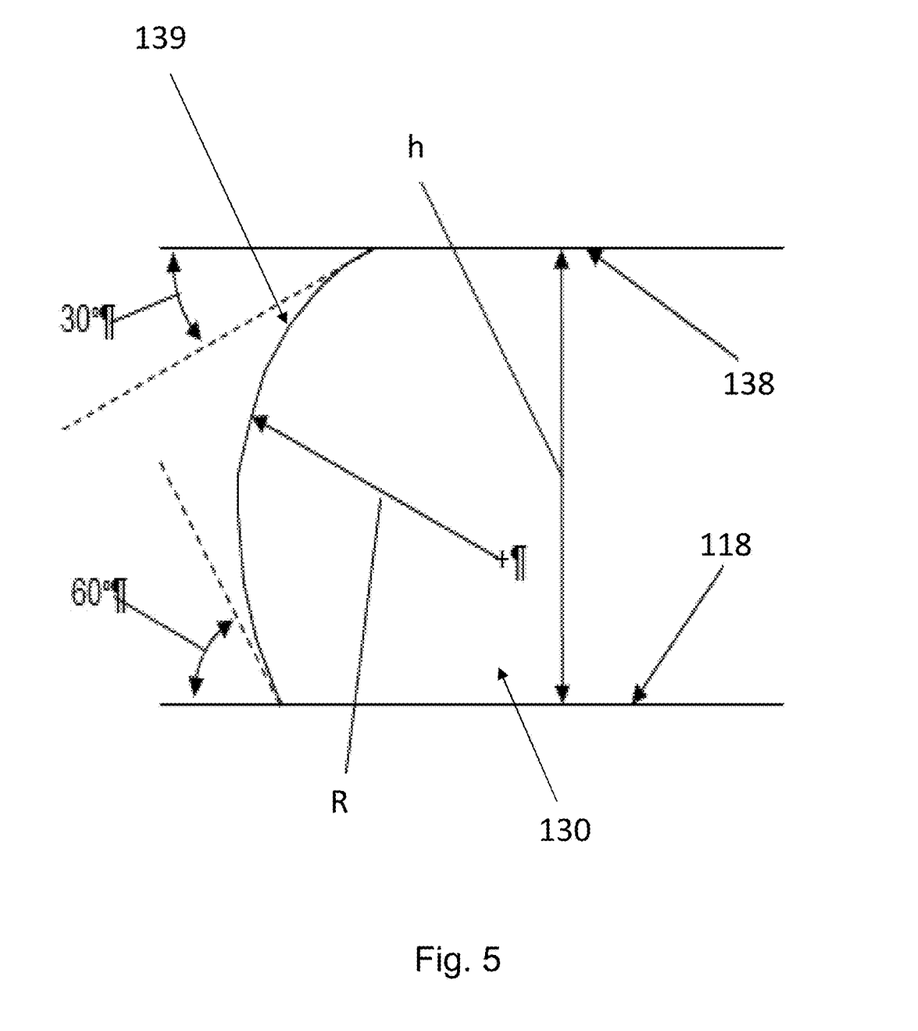
FIG. 5 is a schematic representation of a meniscus of sample in the wicking zone of a lateral flow assay device.

A model can be created of the system shown in FIG. 5, for sizing of the herein described capillary vent, wherein a meniscus 139 of sample fluid transported by the device and more particularly in the wicking zone 130 is depicted. First, the time that is required for the sample fluid to fill a normally vented tube can be expressed as $$t = \frac{V_{wz}}{Q} \quad (1)$$

In which t is time is expressed in seconds, $V_{wz}$ is the volume of the wicking zone, and Q is the average volumetric flow rate of the fluid entering the wicking zone of the herein described assay device 100. The average volumetric flow rate into the wicking zone 130 may be expressed as:

$$Q = C_1 \frac{(p_{cap} - p_{back})}{\mu} \quad (2)$$

in which $p_{cap}$ is the capillary pressure pulling the fluid into the wicking zone, $p_{back}$ is the backpressure generated by the air in the wicking zone flowing through the capillary tube, and $\mu$ is the sample fluid viscosity. $C_1$ is a constant.

For laminar flow through a wide, thin, and long rectangular tube or channel having a constant cross section, the volumetric flow rate can approximated by $$Q = \frac{wh^3}{12\mu_{air}}\left(\frac{\Delta p}{l}\right) \quad (3)$$

in which w is the width of the channel, h is the height (the thin dimension), l is the tube length, μ is the fluid viscosity (air) and Δp is the pressure drop through the tube. By rearranging (3), we obtain $$\Delta p = \frac{12Q\mu_{air}l}{wh^3} = p_{back} \quad (4)$$

Substituting equation (4) into equation (2) and simplifying, we obtain:

$$Q = \frac{c_1 p_{cap} wh^3}{\mu_{air}(wh^3 + 12C_1 l)} \quad (5)$$

$P_{cap}$ can be estimated by examining the sample fluid meniscus shape 139 between the hydrophilic layer 138, FIG. 4, in the wicking zone 130 and the floor 118 of the wicking zone. FIG. 5 depicts a meniscus 139 of sample (blood serum) in the wicking zone 130 for a specific assay device. By analyzing the geometry, the radius of curvature of the meniscus of the blood serum sample can be calculated to be 54.9 μm. As is known from Physiol, Res. 56 (Suppl. 1); S93-S98, 2007, Temperature Dependence of Blood Surface Tension, J. Rosina, et al, an equation to compute the surface tension of blood serum as a function of temperature can be provided as:

$$\sigma_t = (-0.368t + 66.072) \times 10^{-3} \text{ N/m} \quad (6)$$

If t=25° C., $\sigma_{serum}$=0.0569 N/m. Using the Young-Laplace equation, the capillary pressure can then be calculated:

$$\Delta p = \sigma\left(\frac{1}{R_1} + \frac{1}{R_2}\right) = \quad (7)$$
$$0.0569 \frac{N}{m}\left(\frac{1}{\infty} + \frac{1}{5.49 \times 10^{-5} m}\right) = 1036 \text{ N/m}^2 = 4.17'' \text{ H}_2\text{O}$$

Empirically, it can be shown that the resulting capillary pressure of 4.17" of H₂O agrees well with empirical results performed that demonstrate that the wicking zone is easily able to fill itself with the chip oriented vertically (a pressure of a little less than 2" of H₂O).

A value for the constant $C_1$ in Equation 2 can be calculated with a few initial assumptions. In this example, a device substrate having a wicking zone volume of 7 μl (7×10⁻⁹ m³) fills in 240 seconds (4 minutes) with serum having a fluid viscosity of 1.6 cP (0.0016 Ns/m²). This particular device has large wicking zone vents, so $p_{back}$=0

$$C_1 = \quad (8)$$
$$\frac{Q\mu}{(p_{cap} - p_{back})} = \frac{\frac{7 \times 10^{-9} m^3}{240 s} \times 0.0016 \frac{Kg}{ms}}{1036 \frac{N}{m^2}} = 4.5 \times 10^{-17} m^3$$

According to one example for explanation purposes, a capillary vent is to be designed that will take the fill time of the wicking zone from 4 minutes (i.e., the afore noted 240 seconds) to 10 minutes (i.e., 600 seconds). This goal is desirous in order to improve assay sensitivity as well the efficiency of a wash operation in which a wash fluid can be added to the assay device. Assuming that the capillary vent is formed (etched) with a depth as deep as the projections (74 μm=w) formed in the wicking zone of the device, and assuming a capillary vent 10 μm high (h), Equations (1) and (5) can be combined to yield $$l = \frac{tC_1 p_{cap} wh^3 - V_{wz}\mu_{sample} wh^3}{12C_1 V_{wz}\mu_{air}} \quad (9)$$

$$l = \frac{74 \times 10^{-6} m \times (10 \times 10^{-6} m)^3 \times}{(600 s \times 4.5 \times 10^{-17} m^3 -} \quad (10)$$
$$l = \frac{7 \times 10^{-9} m^3 \times 0.0016 \text{ Ns/m}^2)}{12 \times 4.5 \times 10^{-17} m^3 \times 7 \times}$$
$$10^{-9} m^3 \times 1.836 \times 10^{-5} \text{ Ns/m}^2$$

$$l = 0.0179 m = 17.9 mm \quad (11)$$

Therefore, a rectangular capillary vent having a length of 17.9 mm and a height of 10 μm and a width of 74 μm will change the fill time of the defined wicking zone from about 4 minutes to about 10 minutes.

If a sample having a serum viscosity of 2 cp instead of 1.6 cp (average) were encountered, the standard vent design would have a wicking zone fill time of $$t=4 \text{ minutes}*(2/1.6)=5 \text{ minutes} \quad (12)$$

This is a 25% increase in fill time over an average sample.

The corresponding change in the capillary vented design can be calculated by using equation 9 and solving for t (time) substituting the new value for viscosity (2 cp). With this substitution, the wicking zone fill time is calculated to be 660 seconds. This change therefore provides a resulting 10% increase in fill time over that of an average sample. As a result, flow time sensitivity to sample viscosity is improved. In fact, the more dampening (as created by the capillary vent) drives the total time to fill the wicking zone, the less influence that fluid viscosity has on flow. In addition, the slopes of the flow rate curves for both the sample viscosity controlling regime and the vent capillary controlling regime are lower than the alternative controlling mechanisms, meaning that variations in sample or specimen flow rate due to viscosity effects have been minimized.

Figure 6:
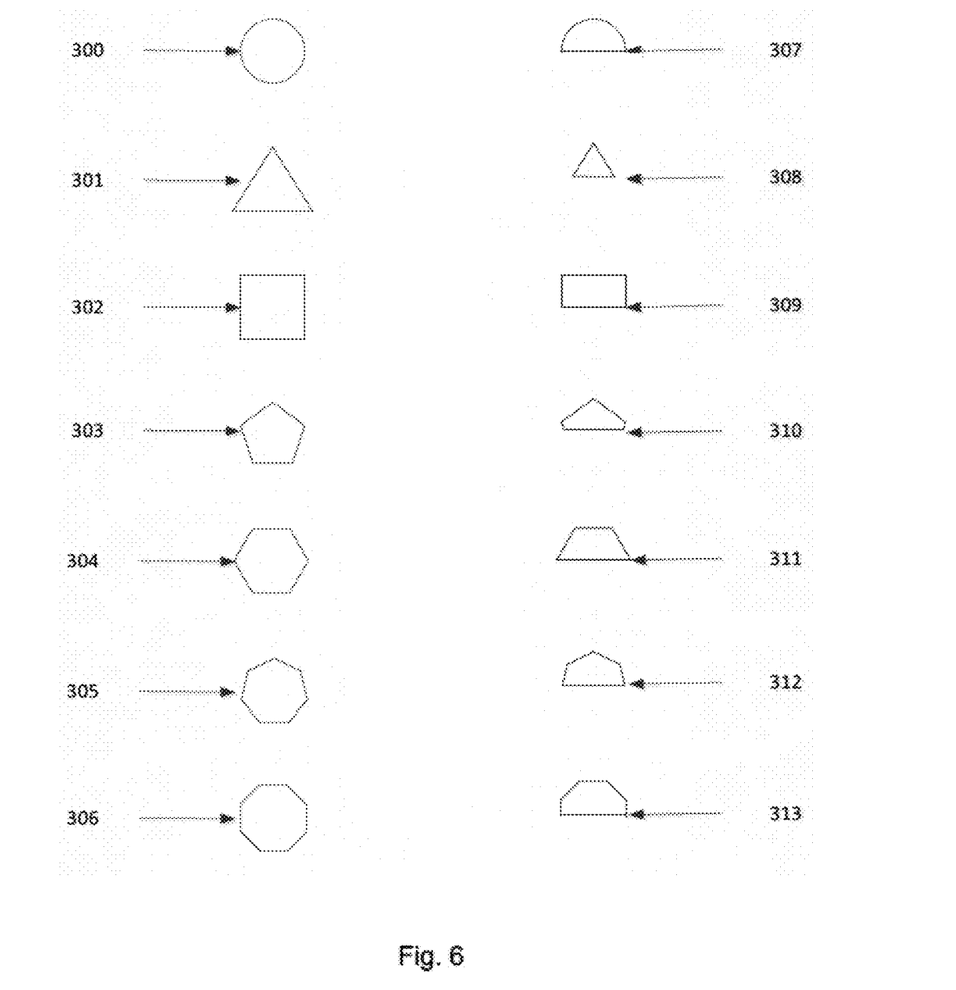
FIG. 6 depicts various cross sectional configurations that can be provided for an air capillary vent, such as that depicted in FIG. 4, depending on the design of the device.

The cross section of the foregoing capillary vent is tubular (circular). However, it should be pointed out that other polygonal shapes can be utilized for useful cross sections of the vent, including but not limited to triangular, quadrilateral, and those of other regular and irregular polygons as shown by way of example in the various depicted versions depicted according to FIG. 6. A number of the provided cross sections are more preferable than others in the instance of a device fabricated by means of injection molding. In the latter instance, certain of the depicted geometries (i.e., cross sections 303, 304, 305, 306 and 310) would cause the molded device could cause undercuts in the fabricated part, creating an issue in which the part could stick to the mold.

Figure 7:
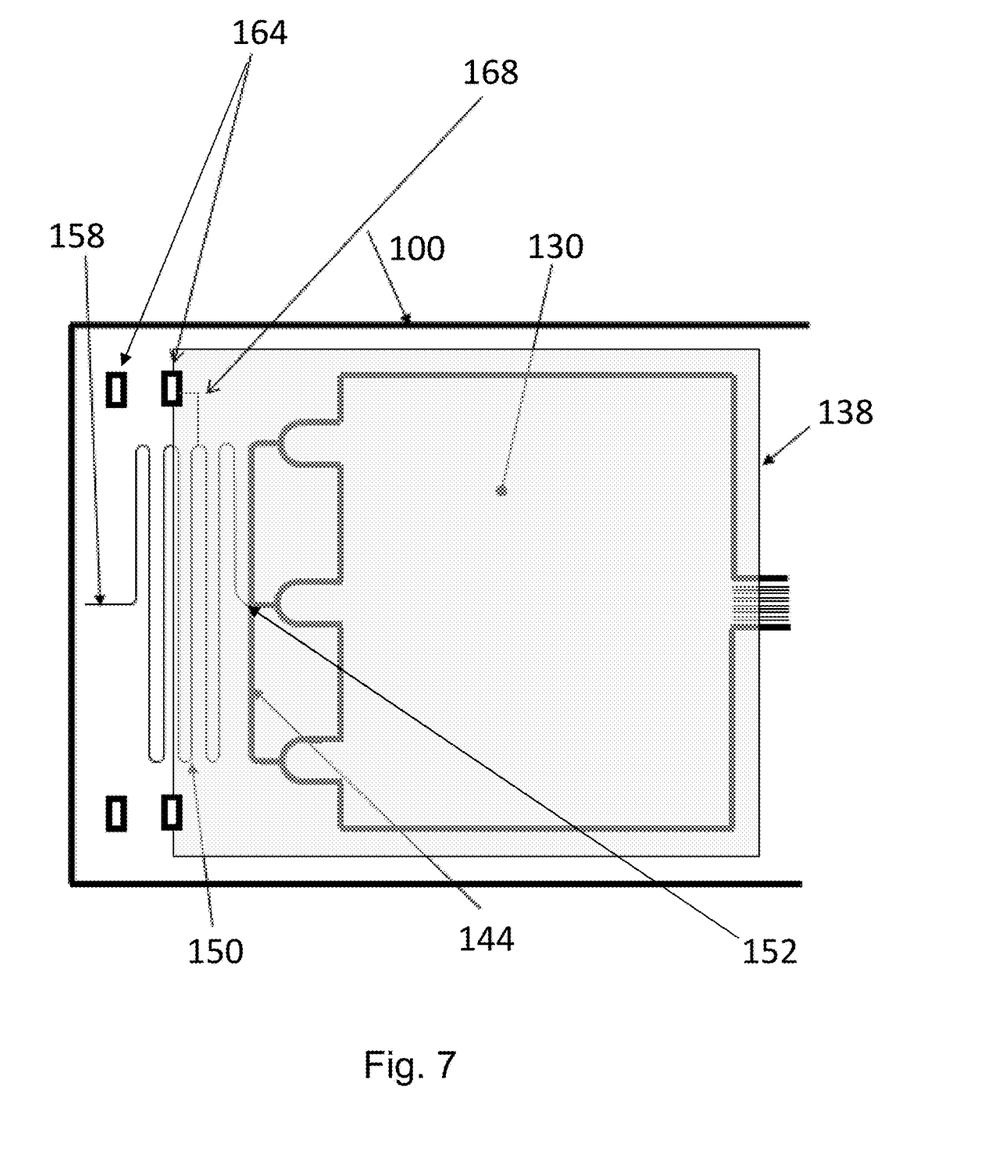
FIG. 7 is a top plan view of an end portion of a lateral flow assay device having at least one feature for adjusting the length of the capillary vent and adjusting the damping characteristics of the assay device.

Advantageously, manipulating the parameters of the capillary tube (conduit or vent) permits the physical configuration of the sample addition zone, the transport and reaction zone and the wicking zone of the lateral flow assay device to remain fixed for different analytical tests, as well as for a plurality of different sample or specimen fluids. For example and with reference to FIG. 7, the position of the hydrophilic layer 138 can be varied using alignment features 164 provided on the top surface of the substrate. As shown herein, inwardly positioning the edge of the hydrophilic cover 138 reduces the effective length of the capillary vent 150 by shifting the exit port 158 to atmosphere closer to the entrance port 148. Optionally, an assay device can be configured with several sets of these alignment or positioning features 164 in order to vary the length of the capillary vent 150, rather than having to redesigning a new substrate for the lateral flow assay device 100. As shown, an additional vent junction 168 can be provided that extends between the capillary vent 150 and the alignment feature 164.

PARTS LIST FOR FIGS. 1-7

1 lateral flow assay device
2 sample addition zone or area
3 reagent area or zone
4 flow channel
5 wicking or absorbing area or zone
7 top surface, substrate
12 projections
20 lateral flow assay device
40 substrate, planar
44 top or upper surface, substrate
48 sample receiving area or zone
52 reagent area or zone
56 detection area
57 flow bridging structure
60 wicking or absorbing area or zone
64 flow channel
70 hydrophilic layer
72 vents
78 positioning feature
100 lateral flow assay device
114 substrate
118 top surface, substrate
127 fluid flow path
129 bridging structure
130 wicking zone
138 hydrophilic layer
139 meniscus, sample
140 vents
144 vent channels
148 entrance port
150 capillary vent
152 entrance port, capillary vent
156 bends, capillary vent
158 exit port, capillary vent
164 alignment features
168 junction, vent
300-313 cross-sectional configurations, capillary vent
h height, wicking zone It will be readily apparent to those of skill in the field that various modifications and variations can be made to the herein described assay device and as covered by the following claims.

The invention claimed is:

1. A lateral flow assay device comprising:
a substrate having a top surface; a liquid sample addition zone for receiving a sample;
a transport and reaction zone;
a wicking zone, each of the liquid sample addition zone, transport and reaction zone and wicking zone being formed in the top surface of the substrate and fluidically interconnected to define at least one fluid flow path extending from the liquid sample addition zone to the wicking zone;
two or more vents at the terminus of the wicking zone; and
a vent channel from each of the two or more vents to a capillary vent;
wherein the capillary vent has an overall length and cross-sectional area that creates a backpressure so as to control the flow rate of a sample applied to the assay device.

2. The assay device as recited in claim 1, wherein the cross section of the capillary vent is circular.

3. The assay device as recited in claim 1, wherein the cross section of capillary vent is one of a circle or a polygon.

4. The assay device as recited in claim 3, wherein the cross section of the capillary vent is one of a regular or irregular polygon.

5. The assay device as recited in claim 1, including a hydrophilic layer covering the wicking zone and the capillary vent.

6. The assay device as recited in claim 1, wherein the capillary vent is defined by a series of bends that are substantially transverse to the fluid flow path entering the wicking zone.

7. The assay device as recited in claim 5, wherein each vent channel has a cross section large enough so as not to create backpressure and forming a manifold.

8. The assay device as recited in claim 5, further including at least one feature for aligning an edge of the hydrophilic layer.

9. The assay device as recited in claim 8, including spaced alignment features to enable the length of the capillary vent to be adjusted.

10. The assay device as recited in claim 1, wherein the capillary vent is sinuous.

11. The assay device as recited in claim 1, wherein the capillary vent includes at least one turn.

12. The assay device as recited in claim 1, wherein the capillary vent includes a path that is not linear.

13. The assay device as recited in claim 1, wherein the overall length is about 17.9 mm.

* * * * *